US005840707A

United States Patent [19]

Mannino et al.

[11] Patent Number: 5,840,707

[45] Date of Patent: Nov. 24, 1998

[54] STABILIZING AND DELIVERY MEANS OF BIOLOGICAL MOLECULES

[75] Inventors: Raphael James Mannino; Susan Gould-Fogerite, both of Annandale, N.J.

[73] Assignees: Albany Medical College, Albany, N.Y.; University of Medicine and Dentistry of New Jersey, Newark, N.J.

[21] Appl. No.: 394,170

[22] Filed: Feb. 22, 1995

Related U.S. Application Data

[63] Continuation-in-part of Ser. No. 130,986, Oct. 4, 1993.

[51] Int. Cl.[6] .................... A61K 9/127

[52] U.S. Cl. .................... 514/44; 514/2; 424/450

[58] Field of Search .................... 424/450; 514/2, 514/44

[56] References Cited

U.S. PATENT DOCUMENTS

| | | |
|---|---|---|
| 4,078,052 | 3/1978 | Papahadjopoulos . |
| 4,663,161 | 5/1987 | Mannino et al. . |
| 4,871,488 | 10/1989 | Mannino et al. . |

OTHER PUBLICATIONS

Booser et al. Anthracycline antibiotics in cancer therapy. Drugs. 1994, vol. 47, No. 2, pp. 223–258.

Mori et al. Immunotargeting of liposomes containing lipophilic antitumor prodrugs. Pharmaceutical 1993. vol. 10, No. 4, pp. 507–514.

Liposome Technology, Second Edition, vol. 1, G. Gregoriadis, Ph.D., "Liposome Preparation and Related Techniques", published 1993 by CRC Press, Inc., (Boca Raton), pp. 67–80.

J. Exp. Med., vol. 176, issued Dec. 1992, M.D. Miller et al., "Vaccination of Rhesus Monkeys with Synthetic . . . CD8+ Cytotoxic T Lymphocytes", pp. 1739–1744.

Nature, vol. 342, issued 30 Nov. 1989, K. Deres et al., "In vivo Priming of Virus–specific Cytotoxic T Lymphocytes with Synthetic Lipopeptide Vaccine", pp. 561–564.

Gene, vol. 84, issued 1989, S. Gould–Fogerite et al., "Chimerasome–mediated Gene Transfer in vitro and in vivo", pp. 429–438.

Biochimica et Biophysica Acta, vol. 394, issued 1975, D. Papahadjopoulos et al., "Cochleate Lipid Cylinders: Formation By Fusion of Unilamellar Lipid Vesicles", pp. 483–491.

Analytical Biochemistry, vol. 148, issued 1985, S. Gould–Fogerite et al., "Rotary Dialysis: Its Application to the Preparation of Membrane Proteins", pp. 15–25.

Biotechniques, vol. 6, No. 7, 1988, Mannino & Gould–Fogerite, "Liposome Mediated Gene Transfer", pp. 682–690.

Advances in Membrane Biochemistry and Bioenergetics, 1988, Gould–Fogerite et al., "The Reconstitution of Biologically . . . Animal Cells", pp. 569–586.

Journal of Immunology, vol. 147, No. 2, 1991, Goodman––Snitkoff et al., "Role of Intrastructural/Intermolecular Help in Immunization with Peptide–Phospholipid Complexes", pp. 410–415.

*Primary Examiner*—Jacqueline M. Stone
*Assistant Examiner*—Patrick Twomey
*Attorney, Agent, or Firm*—Sughrue, Mion, Zinn, Macpeak, and Seas

[57] ABSTRACT

The instant disclosure relates to cochleates comprising a) a biologically relevant molecule component b) a negatively charged lipid component, and c) a divalent cation component. The cochleate has an extended shelf life, even in a desiccated state. Advantageously, the cochleate can be ingested. The biologically relevant molecule can be a polynucleotide.

27 Claims, 8 Drawing Sheets

COCHLEATE

BILAYERS TIGHTLY APPOSED
53Å REPEAT DISTANCE.
APPROXIMATELY 52Å OCCUPIED BY EACH LIPID
BILAYER THEREFORE ONLY 1Å BETWEEN
BILAYERS.
SINGLE Ca ION BRIDGING.
WATER IS EXCLUDED.

PHOSPHATIDYLSERINE

REPEAT DISTANCE
53Å

HYDROPHOBIC
TAIL-ACYL CHAINS

1Å

CALCIUM ION-2 POSITIVE
CHARGES BRIDGED BE-
TWEEN LAYERS, HOLDING
THEM TOGETHER.
COCHLEATE UNFOLDS
WHEN Ca++ IS REMOVED

SINGLE NEGATIVE CHARGE
ON POLAR HEAD GROUP

28Å

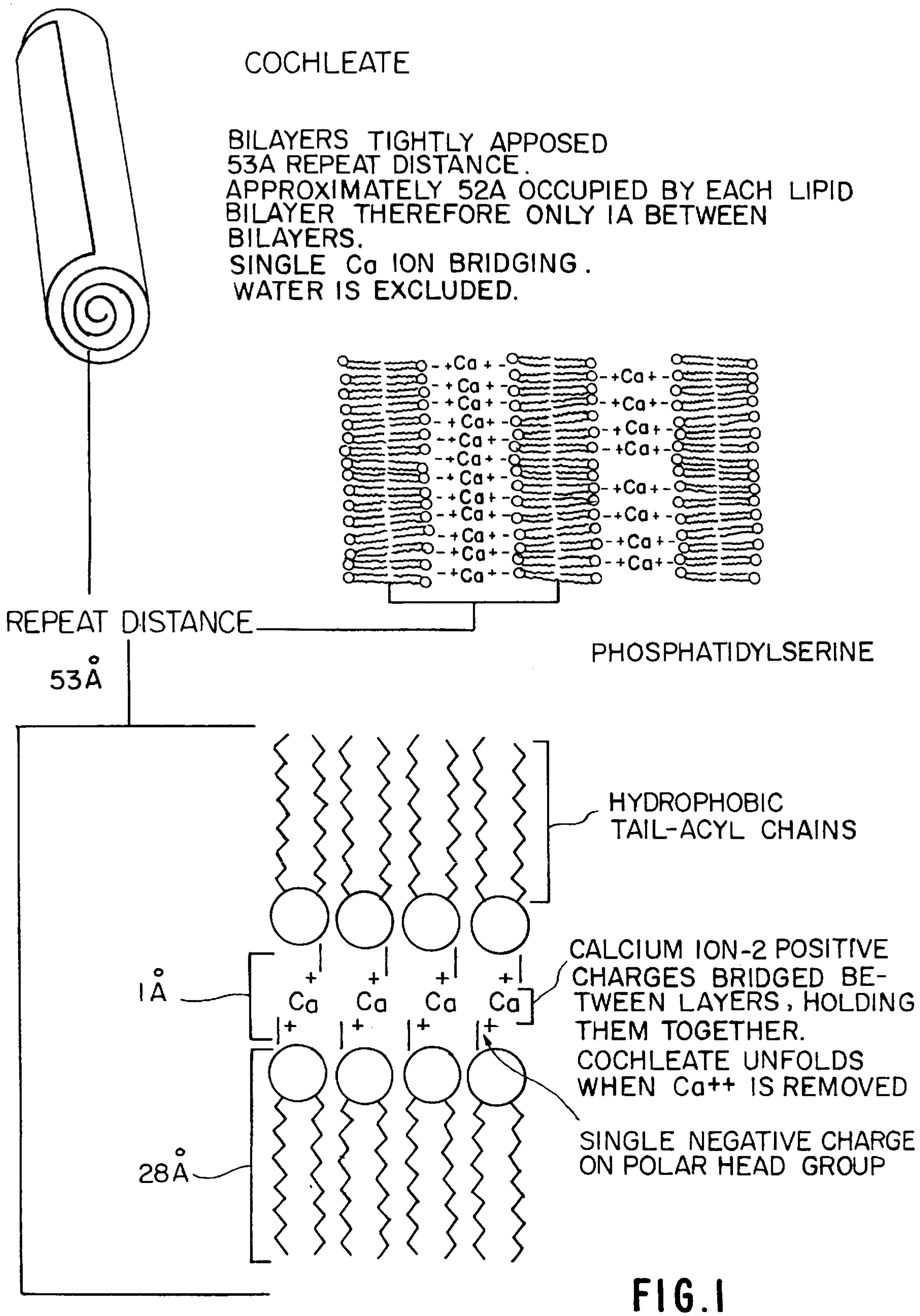

FIG.1

STABILIZING AND DELIVERY MEANS OF BIOLOGICAL MOLECULES

This is a continuation-in-part of application Ser. No. 08/130,986 filed 4 Oct. 1993.

Portions of the subject matter disclosed herein were supported in part by monies or grants from the United States Government.

FIELD OF THE INVENTION

The instant invention relates to cochleates and use thereof to stabilize biologic molecules, such as carbohydrates, vitamins, minerals, polynucleotides, polypeptides, lipids and the like. Cochleates are insoluble stable lipid-divalent cation structures into which is incorporated the biologic molecule. Because cochleates can be biologically compatible, cochleates can be administered to hosts by conventional routes and can serve to deliver the biologic molecule to a targeted site in a host.

BACKGROUND OF THE INVENTION

Plain lipid cochleates (FIG. 1) have been described previously. Protein-cochleates or peptide-cochleates have been described heretofore and patented by the instant inventors, as intermediate structures which can be converted to protein-lipid vesicles (proteoliposomes) (FIG. 2) by the addition of calcium chelating agents (see U.S. Pat. No. 4,663,161 and U.S. Pat. No. 4,871,488, the disclosures of which expressly are incorporated herein by reference). Freeze-fracture electron micrographs of protein-cochleates containing Sendai glycoproteins made by the DC method show the rolled up lipid bilayer structures with a "bumpy" surface. Plain phospholipid cochleates are smooth in that type of preparation.

The proteoliposomes resulting from polypeptide-cochleates have been shown to be effective immunogens when administered to animals by intraperitoneal and intramuscular routes of immunization (G. Goodman-Snitkoff, et al., *J. Immunol.,* Vol. 147, p.410 (1991); M. D. Miller, et al., *J. Exp. Med.,* Vol. 176, p. 1739 (1992)). Further, when the glycoproteins of Sendai or influenza virus are reconstituted by that method, the proteoliposomes are effective delivery vehicles for encapsulated proteins and DNA to animals and to cells in culture (R. J. Mannino and S. Gould-Fogerite, *Biotechniques,* Vol. 6, No. 1, pp. 682–690 (1988); S. Gould-Fogerite et al., *Gene*, Vol. 84, p. 429 (1989); M. D. Miller, et al., *J. Exp. Med.,* Vol. 176, p. 1739 (1992)).

It would be advantageous to provide a means for stabilizing or preserving biologic molecules in a form that is stable at room temperature, capable of desiccation and is suitable for oral administration. For example, it would be beneficial to have a formulation for stabilizing polynucleotides and which could be used for delivering polynucleotides to a cell.

SUMMARY OF THE INVENTION

Accordingly, it is an object of the instant invention to provide a means for stabilizing biologic molecules to yield a formulation with prolonged shelf life, which can be made into powder form and which later can be rehydrated to yield a biologically active molecule.

It also is an object of the instant invention to provide a formulation suitable for use as a vehicle to administer a biologically active molecule to a host. The formulation can be used to deliver a biologic molecule to the gut for absorption or to a targeted organ, tissue or cell.

A suitable biologic molecule is a polynucleotide.

Those and other objects have been obtained by providing a cochleate formulation comprising the following components:

a) a biologically relevant molecule component to be stabilized or delivered, b) a negatively charged lipid component, and c) a divalent cation component.

In a preferred embodiment, the cochleate formulation is administered orally.

The instant invention further provides a cochleate formulation containing a polynucleotide, wherein said polynucleotide-cochleate comprises the following components:

a) a polynucleotide component, b) a negatively charged lipid component, and c) a divalent cation component.

The polynucleotide can be one which is expressed to yield a biologically active polypeptide or polynucleotide. Thus, the polypeptide may serve as an immunogen or, for example, have enzymatic activity. The polynucleotide may have catalytic activity, for example, be a ribozyme, or may serve as an inhibitor of transcription or translation, that is, be an antisense molecule. If expressed, the polynucleotide would include the necessary regulatory elements, such as a promoter, as known in the art.

The advantages of cochleates are numerous. The cochleates have a nonaqueous structure while not having an internal aqueous space, and therefore cochleates:

(a) are more stable than liposomes because the lipids in cochleates are less susceptible to oxidation;

(b) can be stored lyophilized which provides the potential to be stored for long periods of time at room temperatures, which would be advantageous for worldwide shipping and storage prior to administration;

(c) maintain structure even after lyophilization, whereas liposome structures are destroyed by lyophilization;

(d) exhibit efficient incorporation of biological molecules, particularly with hydrophobic moieties into the lipid bilayer of the cochleate structure;

(e) have the potential for slow release of the biologic molecule in vivo as cochleates slowly unwind or otherwise dissociate;

(f) have a lipid bilayer matrix which serves as a carrier and is composed of simple lipids which are found in animal and plant cell membranes, so that the lipids are non-toxic, non-immunogenic and non-inflammatory;

(g) contain high concentration of calcium, an essential mineral;

(h) are safe, the cochleates are non-living subunit formulations, and as a result the cochleates have none of the risks associated with use of live vaccines, or with vectors containing transforming sequences, such as life threatening infections in immunocompromised individuals or reversion to wild type infectivity which poses a danger to even healthy people;

(i) are produced easily and safely; and (j) can be produced as defined formulations composed of predetermined amounts and ratios of biologically relevant molecules, including polypeptides, carbohydrates and polynucleotides, such as DNA.

The advantages of oral administration also are numerous. An oral route has been chosen by the WHO Children's Vaccine Initiative because of ease of administration. Oral vaccines are less expensive and much safer to administer than parenterally (intramuscular or subcutaneous) administered vaccines. The use of needles adds to the cost, and also, unfortunately, in the field, needles are often reused.

BRIEF DESCRIPTION OF THE DRAWINGS

FIG. 1 is a schematic representation of a plain lipid cochleate.

DETAILED DESCRIPTION OF THE INVENTION

Figure 2:
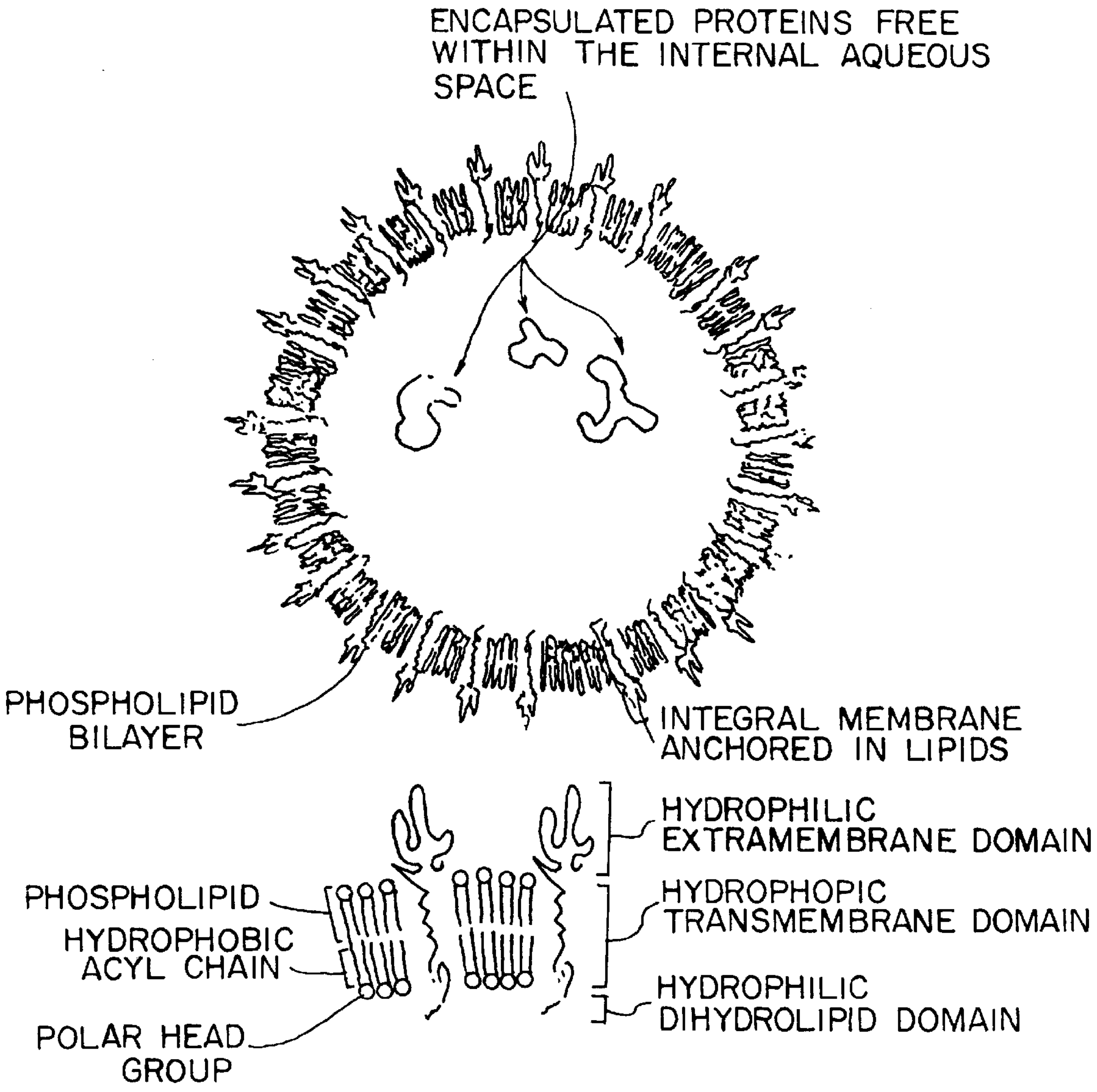
FIG. 2 shows the structure of polypeptide-lipid vesicles with integrated membrane proteins.

The instant inventors have now found surprisingly and have demonstrated that cochleates themselves be used as means for stabilizing and delivering biologic molecules. The cochleates survive the harsh acid environment of the stomach, protecting the susceptible biologic molecules immersed therein, probably by virtue of their unique multilayered precipitate structure. It is likely that cochleates then are taken up by microfold cells (M cells) in the small intestine.

The instant inventors have demonstrated that oral administration by drinking cochleates containing the glycoproteins and viral lipids from the surface of influenza or Sendai viruses plus phosphatidylserine and cholesterol, stimulate both mucosal and circulating antibody responses. In addition, strong helper cell (proliferative) and killer (cytotoxic) cell responses also are generated. Perhaps most impressively, oral administration of the influenza cochleates protects against intranasal challenge with live virus.

Those results are unexpected for a number of reasons.

It was not known and was not expected that the cochleates would survive the stomach and protect the polypeptides associated with them from the acid environment and degradative enzymes. It is known that without the presence of at least 3 mM calcium, the cochleates begin to unwind and form liposomes. It was possible, in fact likely, that the cochleates would not remain intact during the transit from the mouth, down the esophagus and through the stomach. If cochleates did come apart, they would be digested as food.

Also, having survived the stomach, that the cochleates would interact in an effective way with the mucosal and circulating immune systems was unknown and unexpected. Everyone ingests large quantities of proteins, fats and sugars on a daily basis which simply get digested and used as fuel, without stimulating any kind of mucosal or circulating immune responses. Thus, the cochleates deliver molecules which retain biologic activity at the delivery site within the host.

As used herein, the term "immune response" means either antibody, cellular, proliferative or cytotoxic activities, or secretion of cytokines.

Also, as used herein, the term "antigen" is meant to indicate the polypeptide to which an immune response is directed or an expressible polynucleotide encoding that polypeptide.

"Polynucleotide" includes DNA or RNA, as well as antisense and enzymatically active molecules. Thus the biologically relevant molecule can be the polynucleotide itself, the transcript thereof or the translated polypeptide encoded thereby.

A "biologically relevant molecule" is one that has a role in the life processes of a living organism. The molecule may be organic or inorganic, a monomer or a polymer, endogenous to a host organism or not, naturally occurring or synthesized in vitro and the like. Thus, examples include, vitamins, minerals, amino acids, co-factors, enzymes, polypeptides, polypeptide aggregates, polynucleotides, lipids, carbohydrates, nucleotides, starches, pigments, fatty acids, viruses, organelles, steroids and other multi-ring structures, saccharides, metals, metabolic poisons, drugs and the like.

The instant invention also can be praticed using whole cells other subcellular replicative entities, such as viruses and viroids. Hence, bacteria, yeasts, cell lines, viruses and the like can be mixed with the relevant lipid solution, caused to precipitate to yield structures wherein the cells and the like are fixed within the cochleate structure.

Recent studies indicate that the direct injection of DNA plasmids can lead to the expression of the proteins encoded by those plasmids resulting in humoral and cell mediated immune responses, see, for example, Wang et al., *Proc. Natl Acad. Sci.* 90: 4156–4160 (1993); Zhu et al., *Science* 261: 209–211 (1993). Those studies indicate that DNA vaccines could provide a safe and effective alternative for human vaccination. Those studies also suggest that DNA vaccines could benefit from simple, more efficient delivery systems.

The use of lipids to facilitate the delivery, entry and expression of DNA in animal cells is well documented, see, for example, Philip et al., *Mol. Cell Biol.* 14: 2411–2418 (1994). Indeed, DNA-lipid complexes currently form the basis for a number of human gene therapy protocols.

Because cochleates are stable structures which can withstand a variety of physiologic conditions, cochleates are suitable means for delivering biologic molecules, such as, polypeptides or polynucleotides, to a selected site in a host. The polypeptide or polynucleotide is incorporated into and integral with the cochleate structure. Thus the polypeptide or polynucleotide, which may need to be expressed, are protected from degrading proteases and nucleases.

The cochleates used in the instant invention can be prepared by known methods such as those described in U.S. Pat. No. 4,663,161, filed 22 Apr. 1985, U.S. Pat. No. 4,871,488, filed 13 Apr. 1987, S. Gould-Fogerite et al., *Analytical Biochemistry,* Vol. 148, pages 15–25 (1985); S. Gould-Fogerite et al., *Advances in Membrane Biochemistry and Bioenergetics,* edited by Kim, C. H., Tedeschi, T., Diwan, J. J., and Salerno, J. C., Plenum Press, New York, pages 569–586 (1988); S. Gould-Fogerite et al., *Gene,* Vol. 84, pages 429–438 (1989); *Liposome Technology,* 2nd Edition, Vol. I, Liposome Preparation and Related Techniques, Vol. II, Entrapment of Drugs and Other Materials, and Vol. III, Interactions of Liposomes with the Biological Milieu, all edited by Gregory Gregoriadis (CRC Press, Boca Raton, Ann Arbor, London, Tokyo), Chapter 4, pp 69–80, Chapter 10, pp 167–184, and Chapter 17, pp. 261–276 (1993); and R. J. Mannino and S. Gould-Fogerite, Liposome Mediated Gene Transfer, *Biotechniques,* Vol. 6, No. 1 (1988), pp. 682–690.

The polynucleotide can be one which expresses a polypeptide, that is, pathogen membrane polypeptides, aberrant or atypical cell polypeptides, viral polypeptides and the like, which are known or which are suitable targets for host immune system recognition in the development of immunity thereto.

The polynucleotide may express a polypeptide which is biologically active, such as, an enzyme or structural or housekeeping protein.

Also, the polynucleotide may be one which necessarily is not expressed as a polypeptide but nevertheless exerts a biologic effect. Examples are antisense molecules and RNA's with catalytic activity. Thus, the expressed sequence may on transcription produce an RNA which is complementary to a message which, if inactivated, would negate an undesired phenotype, or produce an RNA which recognizes specific nucleic acid sequences and cleaves same at or about that site and again, the non-expression of which would negate an undesired phenotype.

The polynucleotide need not be expressed but may be used as is. Thus, the polynucleotide may be an antisense molecule or a ribozyme. Also, the polynucleotide may be an immunogen.

Thus, for polynucleotides, the relevant coding sequence is subcloned downstream from a suitable promoter, other regulatory sequences can be incorporated as needed, in a vector which is expanded in an appropriate host, practicing methods and using materials known and available in the art.

For example, two plasmids, pDOLHIVenv (AIDS Research and Reference Reagent Program, Jan. 1991 catalog p. 113; Freed et al. *J. Virol.* 63: 4670 (1989)) and pCMVHIVLenv (Dr. Eric Freed, Laboratory of Molecular Immunology, NJAID, NIH) are suitable expression plasmids for use in polynucleotide-cochleates.

The plasmids contain the open reading frames for the env, tat and rev coding regions of HIV-1 (LAV strain).

pDOLHIVenv was constructed by introducing the SalI-XhoI fragment from the full length infectious molecular clone pNL4-3 into the SalI site of the retrovirus vector, pDOL (Korman et al. *Proc. Natl. Acad. Sci.* 84: 2150 (1987)). Expression is from the Moloney murine virus LTR.

pCMVHIVLenv was constructed by cloning the same SalI-XhoI fragment into the XhoI site of the cytomegalovirus (CMV)-based expression vector p763.

The polynucleotide can be configured to encode multiple epitopes or epitopes conjugated to a known immunogenic peptide to enhance immune system recognition, particularly if an epitope is only a few amino acids in size.

To form cochleate precipitates, a majority of the lipid present should be negatively charged. One type of lipid can be used or a mixture of lipids can be used. Phosphatidylserine or phosphatidylglycerol generally have been used. Phosphatidylinositol also forms a precipitate which converts to liposomes on contact with EDTA. A substantial proportion of the lipid can, however, be neutral or positively charged. The instant inventors have included up to 40 mol % cholesterol based on total lipid present and routinely make polypeptide-lipid or polynucleotide-lipid cochleates which contain 10 mol % cholesterol and 20% viral membrane lipids. Phosphatidylethanolamine, plain or cross-linked to polypeptides, also can be incorporated into cochleates.

While negatively charged lipid can be used, a negatively charged phospholipid is preferred, and of those phosphatidylserine, phosphatidylinositol, phosphatidic acid and phosphatidylglycerol are most preferred.

One skilled in the art can determine readily how much lipid must be negatively charged by preparing a mixture with known concentrations of negative and non-negative lipids and by any of the procedures described herein, determining whether precipitates form.

Figure 3:
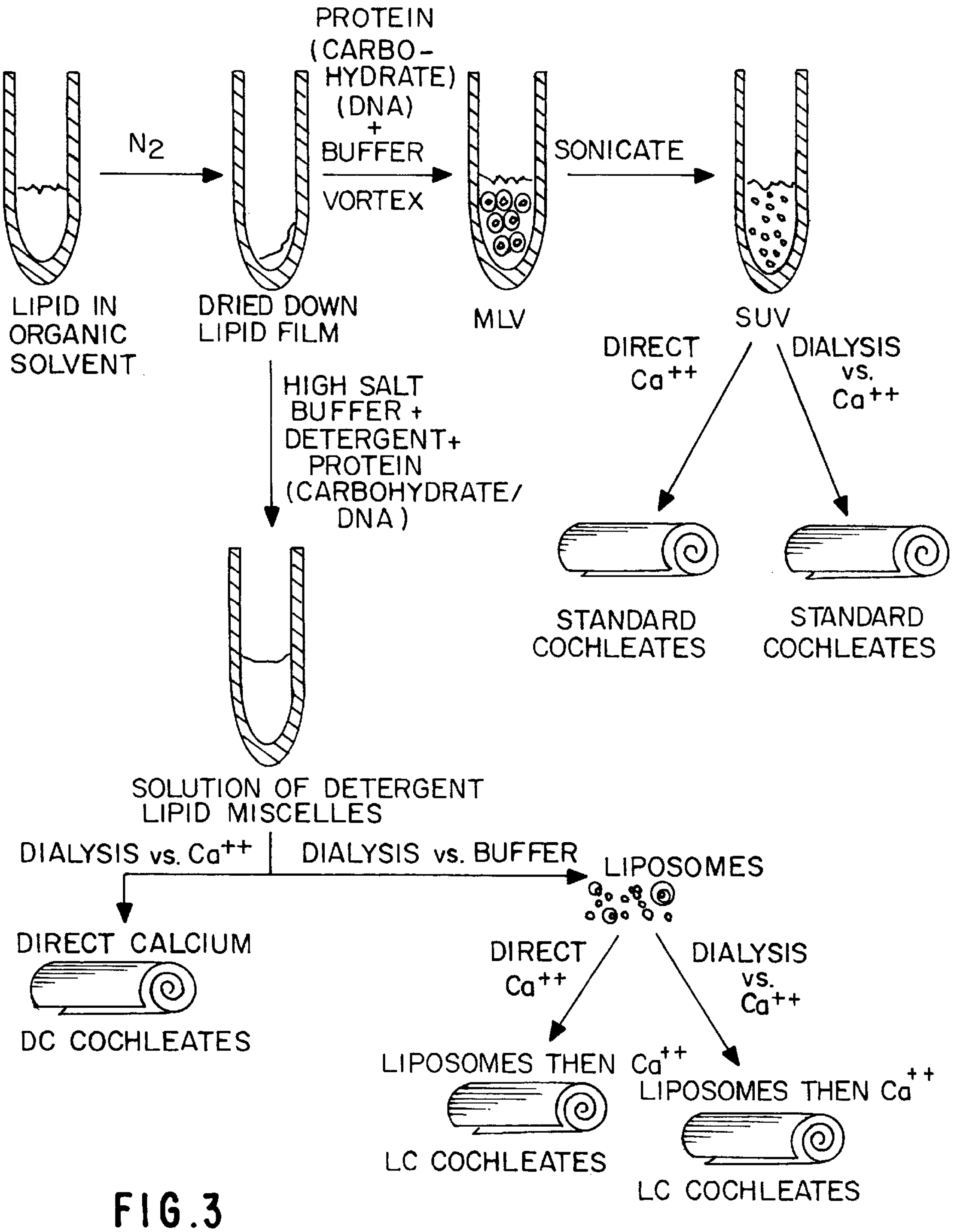
FIG. 3 summarizes the various alternative procedures for the preparation of cochleates.

There are several known procedures for making the cochleates of the instant invention and those are schematized in FIG. 3.

A suitable procedure for making cochleates is one wherein a negatively charged lipid such as phosphatidylserine, phosphatidylinositol, phosphatidic acid or phosphatidylglycerol in the absence or presence of cholesterol (up to 3:1, preferably 9:1 w/w) are utilized to produce a suspension of multilamellar lipid vesicles containing or surrounded by a biologically relevant molecule (polypeptide, polysaccharide or polynucleotide, such as DNA) which are converted to small unilamellar protein lipid vesicles by sonication under nitrogen. Alternatively, to avoid damage, the biologically relevant molecule can be added to the solution following sonication. The vesicles are dialyzed at room temperature against buffered divalent cation, e.g., calcium chloride, resulting in the formation of an insoluble precipitate which may be presented in a form referred to as a cochleate cylinder. After centrifugation, the resulting pellet can be taken up in buffer to yield the cochleate solution utilized in the instant invention.

In an alternative and preferred embodiment, an amount of negatively charged lipid, e.g., phosphatidylserine and cholesterol in the same proportions as above and equal to from about 1 to 10 times the weight, preferably equal to four times the weight of the viral or other additional lipids are utilized to prepare the cochleates. Either a polypeptide, mineral, vitamin, carbohydrate or polynucleotide, such as DNA, is added to the solution. That solution then is dialyzed against buffered divalent cation, e.g., calcium chloride, to produce a precipitate which can be called a DC (for direct calcium dialysis) cochleate.

An additional, related method for reconstituting cochleates has been developed and is called the LC method (liposomes before cochleates). The initial steps involving addition of extracted polypeptide, polysaccharide, polynucleotide, such as DNA or combinations thereof, to dried down negatively charged lipid and cholesterol are the same as for the DC method. However, the solution next is dialyzed against buffer (e.g., 2 mM TES, 2 mM L-histidine, 100 mM NaCl, pH 7.4) to form small liposomes containing the polypeptide, polynucleotide, such as DNA, and/or polysaccharide. A divalent cation, e.g., calcium, then is added either directly or by dialysis to form a precipitate which can consist of cochleates.

In the above procedures for making the cochleates of the instant invention, the divalent cation can be any divalent cation that can induce the formation of a cochleate or other insoluble lipid-antigen structures. Examples of suitable divalent cations include $Ca^{++}$, $Mg^{++}$, $Ba^{++}$, and $Zn^{++}$ or other elements capable of forming divalent ions or other structures having multiple positive charges capable of chelating and bridging negatively charged lipids.

The amount of biologically relevant molecule incorporated into the cochleates can vary. Because of the advantageous properties of cochleates generally, lesser amounts of biologically relevant molecule can be used to achieve the same end result as compared to using known delivery means.

An artisan can determine without undue experimentation the optimal lipid:biologically relevant molecule ratio for the targeted purposes. Various ratios are configured and the progress of precipitation of each sample is monitored visually under a phase contrast microscope. Precipitation to form, for example, cochleates, is monitored readily. Then, the precipitates can be administered to the targeted host to ascertain the nature and tenor of the biologic response to the administered cochleates.

It should be evident that the optimized ratio for any one use may range from a high ratio, for example, to minimize the use of a rare biologically relevant molecule, to a low ratio to obtain maximal amount of biologically relevant molecule in the cochleates.

Cochleates can be lyophilized and stored at room temperature indefinitely or can be stored in a divalent cation-containing buffer at 4° C. for at least six months.

The cochleate formulations also can be prepared both with and without fusogenic molecules, such as Sendai virus envelope polypeptides. Prior studies with proteoliposomes have demonstrated that cytoplasmic delivery of liposome contents requires a fusogenic liposome bilayer. The exact role of Sendai virus envelope polypeptides in facilitating the immune response to polypeptide-cochleates as yet is not clear.

It is preferred to use cochleates without fusogenic molecules over fusogenic molecule cochleates because of a more simple structure and ease of preparation favors eventual use in humans.

Because polynucleotides are hydrophilic molecules and cochleates are hydrophobic molecules that do not contain an internal aqueous space, it is surprising polynucleotides can be integrated into cochleates. The polynucleotides are not exposed on the surface of the cochleates because the polynucleotides are resistant to nucleases.

In the case of polynucleotide cochleates, considerations for dosage parallel the standard methodologies regarding vaccines as known in the art. Also, methods for using polynucleotides in liposomes and the "naked DNA" are available to serve as a baseline for empirically determining a suitable dosing regimen, practicing known methods.

For example, a suitable scheme for determining dosing is as follows.

The initial dose of polynucleotides in cochleates administered by injection to animals is selected to be about 50 μg, although it is know that as little as 2 μg of tested plasmids is effective. That dose is proposed to maximize the probability of observing a positive response following a single administration of a cochleate. Any formulations which do not elicit a response at that dose are to be considered ineffective but retained for further study.

Developing formulations which can be administered easily and non-invasively is desirable. Thus, PO administration of cochleates will be targeted and higher doses will be tried initially (100 μg/animal and 200 μg/animal). However, lower doses are required for parenteral routes.

Then graded doses will be used to develop a dose response curve for each formulation. Thus, cochleates containing 50 μg, 10 μg, 2 μg, 0.4 and 0 μg polynucleotide/animal will be inoculated with at least 10 animals per group.

Immune response or enzymatic activity are responses easily monitored when expression of the polynucleotide is required. Altered phenotype is another response for tracking efficacy of antisense or ribozyme type molecules. In the case of immune system monitoring, T cell proliferation, CTL and antibody presence at specific body sites can be evaluated, using known methods, to assess the state of specific immune response.

To determine the duration of activity of cochleate formulations, groups which have responded to a single immunization are monitored periodically for up to a year or more to determine the effective life of a cochleate on administration.

Animals which fail to develop a detectable response on first exposure can be re-inoculated (boosted) to provide insights into the ability of the low dose formulations to prime the immune system for later stimulation.

Pharmaceutical formulations can be of solid form including tablets, capsules, pills, bulk or unit dose powders and granules or of liquid form including solutions, fluid emulsions, fluid suspensions, semisolids and the like. In addition to the active ingredient, the formulation would comprise suitable art-recognized diluents, carriers, fillers, binders, emulsifiers, surfactants, water-soluble vehicles, buffers, solubilizers and preservatives.

The skilled artisan can determine the most efficacious and therapeutic means for effecting treatment practicing the instant invention. Reference can also be made to any of numerous authorities and references including, for example, "Goodman & Gilman's, The Pharmaceutical Basis for Therapeutics", (6th Ed., Goodman, et al., eds., MacMillan Publ. Co., New York, 1980).

The cochleates of the instant invention can be used as a means to transfect cells with an efficacy greater than using currently known delivery means, such as liposomes. Hence, the polynucleotide cochleates of the instant invention provide a superior delivery means for the various avenue of gene therapy, Mulligan, *Science* 260: 926–931 (1993). As Mulligan noted, the many possibilities of treating disease by gene-based methods will be enhanced by improved methods of gene delivery.

The cochleates of the instant invention also serve as excellent means for delivering other biologically relevant molecules to a host. Such biologically relevant molecules include nutrients, vitamins, co-factors, enzymes and the like. Because the biologically relevant molecule is contained within the cochleate, in a non-aqueous environment, the biologically relevant molecule essentially is stabilized and preserved. As described hereinabove, the biologically relevant molecule is added to the lipid solution and processed to form a precipitated structure comprising lipid and biologically relevant molecule. As demonstrated herein, hydrophilic molecules can be "cochleated", that is, can be made part of the cochleate structure, with little difficulty.

The instant invention now will be described by means of specific examples which are not meant to limit the invention.

EXAMPLE 1

Bovine brain phosphatidylserine in chloroform was purchased from Avanti Polar Lipids, Birmingham, Ala. in glass ampules and stored under nitrogen at −20° C. Cholesterol (porcine liver) grade I, β-D-octyl-glucopyranoside, fluorescein isothiocyanate (FITC)-dextran (average mol. wt. 67,000), metrizamide grade I, and chemicals for buffers and protein and phosphate determinations, were obtained from Sigma Chemical Company, St. Louis, Mo. Organic solvents were purchased from Fisher Scientific Co., Fairlawn, N.J. Reagents for polyacrylamide gel electrophoresis were from BioRad Laboratories, Richmond, Calif. S1000 Sephacryl Superfine was obtained from Pharmacia, Piscataway, N.J. Thick walled polycarbonate centrifuge tubes (10 ml capacity) from Beckman Instruments, Palo Alto, Calif., were used for vesicle preparations, washes, and gradients. A bath type sonicator, Model G112SP1G, from Laboratory Supplies Company, Hicksville, N.Y. was used for sonications.

Virus was grown and purified essentially as described by M. C. Hsu et al., *Virology,* Vol. 95, page 476 (1979). Sendai (parainfluenza type I) and influenza (A/PR8/34) viruses were propagated in the allantoic sac of 10 or 11 day old embryonated chicken eggs. Eggs were inoculated with 1–100 egg infectious doses ($10^3$ to $10^5$ viral particles as determined by HA titer) in 0.1 ml of phosphate buffered saline (0.2 gm/L KCl, 0.2 gm/L $KH_2PO_4$, 8.0 gm/L NaCl, 1.14 gm/L $Na_2H—PO_4$, 0.1 gm/L $CaCl_2$, 0.1 gm/L $MgCl_26H_2O$ (pH 7.2)). Eggs were incubated at 37° C. for 48 to 72 hours, followed by incubation at 4° C. for 24 to 48 hours. Allantoic fluid was collected and clarified at 2,000 rpm for 20 minutes at 5° C. in a Damon IEC/PR-J centrifuge. The supernatant was then centrifuged at 13,000 rpm for 60 minutes. This and all subsequent centrifugations were performed in a Sorvall RC2-B centrifuge at 5° C. using a GG rotor. The pellets were resuspended in phosphate buffered saline (pH 7.2) by vortexing and sonicating, followed by centrifugation at 5,000 rpm for 20 minutes. The pellet was resuspended by vortexing and sonicating, diluting, and centrifuging again at 5,000 rpm for 20 minutes. The two 5,000 rpm supernatants were combined and centrifuged at 13,000 rpm for 60 minutes. The resulting pellets were resuspended in phosphate-buffered saline by vortexing and sonicating, aliquoted, and stored at −70° C. Sterile technique and materials were used throughout viral inoculation, isolation, and purification.

Virus stored at −70° C. was thawed, transferred to sterile thick-walled polycarbonate tubes and diluted with buffer A (2 mM TES, 2 mM L-histidine, 100 mM NaCl (pH 7.4)). Virus was pelleted at 30,000 rpm for 1 hour at 5° C. in a Beckman TY65 rotor. The supernatant was removed and the pellet resuspended to a concentration of 2 mg viral protein per ml of extraction buffer (2M NaCl, 0.02M sodium phosphate buffer (pH 7.4)) by vortexing and sonicating. The nonionic detergent β-D-octyl-glucopyranoside was then added to a concentration of 2% (w/v). The suspension was mixed, sonicated for 5 seconds and placed in a 37° C. water bath for 45 minutes. At 15, 30 and 45 minute incubation times, the suspension was removed briefly for mixing and sonication. Nucleocapsids were pelleted by centrifugation at 30,000 rpm for 45 minutes in a TY65 rotor. The resulting clear supernatant was removed and used in the formation of viral glycoprotein-containing cochleates. Some modification of the above procedure may have to be employed with other membrane proteins. Such modifications are well known to those skilled in the art.

EXAMPLE 2

A. DC Cochleates.

An amount of phosphatidylserine and cholesterol (9:1 wt ratio) in extraction buffer and non-ionic detergent as described hereinabove was mixed with a pre-selected concentration of polynucleotide and the solution was vortexed for 5 minutes. The clear, colorless solution which resulted was dialyzed at room temperature against three changes (minimum 4 hours per change) of buffer A (2 mM TES N-Tris[hydroxymethyl]-methyl-2 aminoethane sulfonic acid, 2 mM L-histidine, 100 mM NaCl, pH 7.4) containing 3 mM $CaCl_2$. The final dialysis routinely used is 6 mM $Ca^{2+}$, although 3 mM $Ca^{2+}$ is sufficient and other concentrations may be compatible with cochleate formation. The ratio of dialyzate to buffer for each change was a minimum of 1:100. The resulting white calcium-phospholipid precipitates have been termed DC cochleates. When examined by light microscopy (×1000, phase contrast, oil), the suspension contains numerous particulate structures up to several microns in diameter, as well as needle-like structures.

B. LC Cochleates.

An amount of phosphatidylserine and cholesterol (9:1 wt ratio) in extraction buffer and non-ionic detergent as described hereinabove was mixed with a pre-selected concentration of polynucleotide and the solution was vortexed for 5 minutes. The solution first was dialyzed overnight using a maximum ratio of 1:200 (v/v) of dialysate to buffer A without divalent cations, followed by three additional changes of buffer leading to the formation of small protein lipid vesicles. The vesicles were converted to a cochleate precipitate, either by the direct addition of $Ca^{2+}$ ions, or by dialysis against two changes of buffer A containing 3 mM $Ca^{2+}$ ions, followed by one containing buffer A with 6 mM $Ca^{2+}$.

EXAMPLE 3

Immune Responses to Orally Delivered Protein-cochleate Vaccines

To make the vaccine, influenza virus was grown, purified, and the glycoproteins and lipids extracted and isolated as described in Example 1. Protein-cochleates were made according to the "LC cochleate" procedure described above.

Figure 4A:
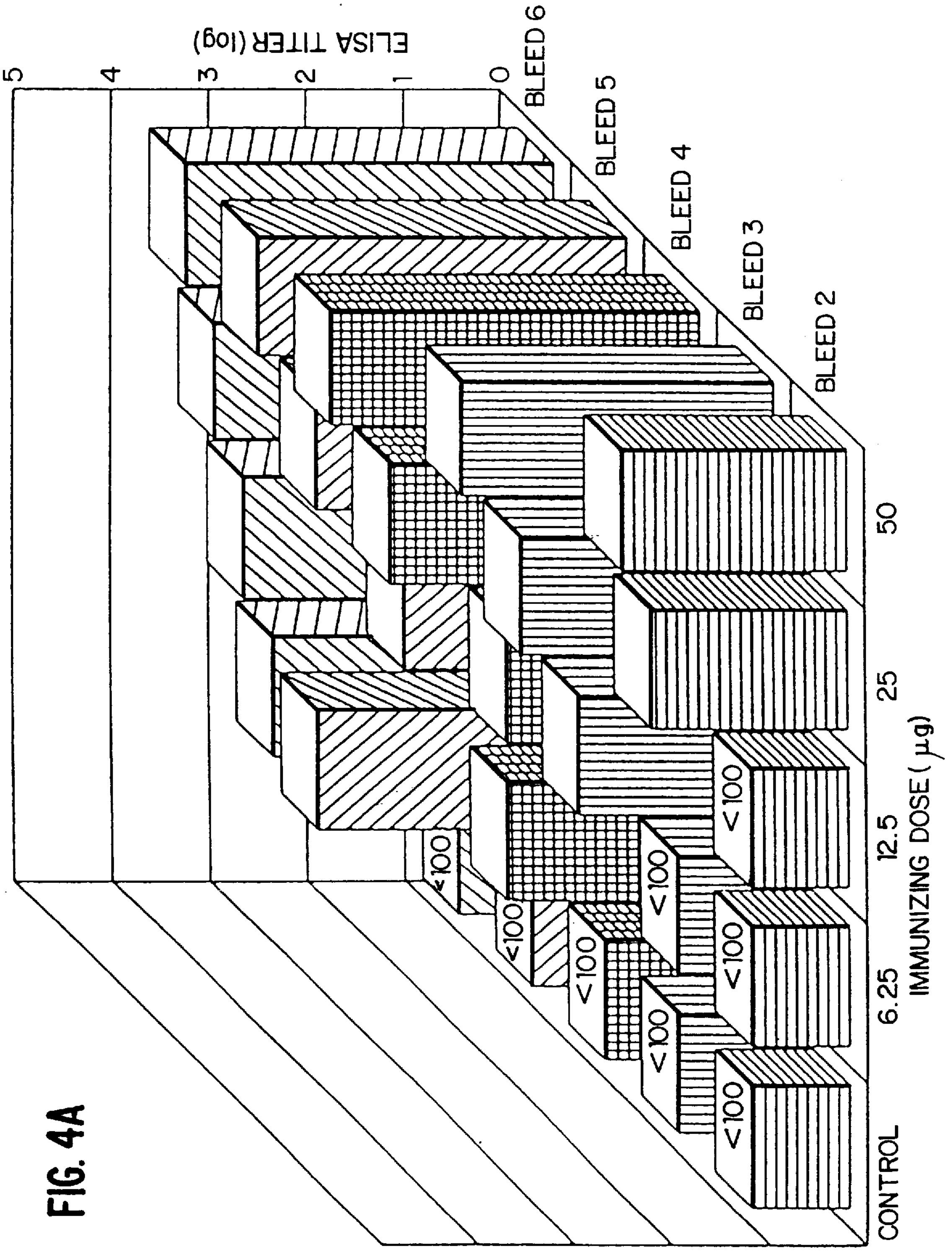
FIGS. 4(A) and 4(B) show serum antibody titers in mice following oral administration of influenza polypeptide-cochleates.

Cochleate vaccines containing the glycoproteins and lipids from the envelope of influenza virus and phosphatidylserine and cholesterol were given to mice by gradually dispensing 0.1 ml liquid into the mouth and allowing it to be comfortably swallowed. FIGS. 4(A) (from Experiment A) and 4(B) (from Experiment B) show resulting total circulating antibody levels specific for influenza glycoproteins, as determined by ELISA. Antibody titer is defined as the highest dilution that still gives the optimal density of the negative control.

In Experiment A that generated the data shown in FIG. 4(A), initial vaccine doses of 50, 25, 12.5 or 6.25 μg of glycoproteins (groups 1 through 4 respectively) were administered at 0 and 3 weeks. The third and fourth immunizations (6 and 19 weeks) were at one fourth the dose used for the initial two immunizations. Bleed 1–Bleed 6 occurred at 0, 3, 6, 9, 19, and 21 weeks. The data demonstrate that high circulating antibody titers can be achieved by simply drinking cochleate vaccines containing viral glycoproteins. The response is boostable, increasing with repeated administration, and is directly related to the amount of glycoprotein in the vaccine.

Figure 4B:
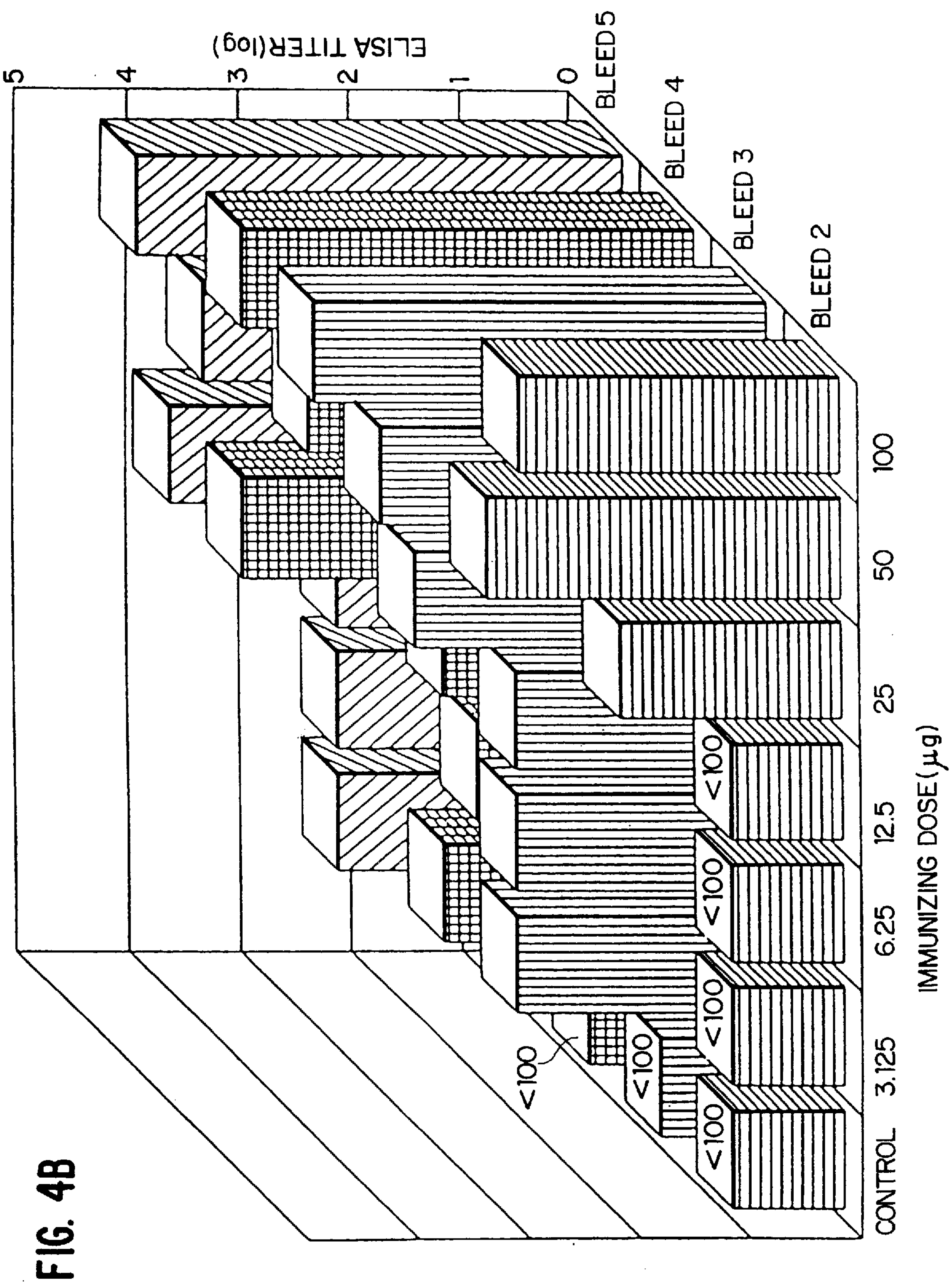

Those observations were confirmed and extended in Experiment B that generated the data shown in FIG. 4(B). The dose range was expanded to include 100 μg and 3.1 μg initial doses. Vaccine was given at 0, 3 and 15 weeks, with the third immunization at one fourth the dose of the initial two. Bleed 1 to Bleed 6 occurred at 0, 3, 6, 15 and 16 weeks. Circulating influenza glycoprotein-specific responses were detectable after a single administration for the top five doses, and for all groups after two feedings. The data shown is for pooled sera from each group, but all mice given the four highest doses, and four of five mice in groups five and six, responded to the vaccine with circulating antibody titers ranging from 100 to 102,400. Group seven, which received no vaccine, had titers less than 50 for all mice at all time points.

The antibody response is long lived. Titers 13 weeks after the third immunization (FIG. 4(A), bleed 5) and 12 weeks after the second immunization (FIG. 4(B), bleed 4) remained the same or within one dilution higher or lower than seen at 3 weeks after the previous boost.

To determine whether oral administration of the subunit vaccine described in Example 2 could lead to protective immunity in the respiratory tract, the mice described in Experiment B of Example 2 were immunized with cochleates at 0, 3 and 15 weeks. The immunized mice were challenged by intranasal application of $2.5\times10^9$ particles of influenza virus at 16 weeks. Three days after viral challenge, mice were sacrificed, and lungs and trachea were obtained. The entire lung or trachea was triturated and sonicated, and aliquots were injected into embryonated chicken eggs to allow amplification of any virus present. After three days at 37° C., allantoic fluid was obtained from individual eggs and hemagglutination (HA) titers were performed.

Mice were also challenged with live influenza intranasally following oral cochleate administration in Experiment A of Example 2. Lungs were obtained three days later and cultured to detect presence of virus.

Figure 5:
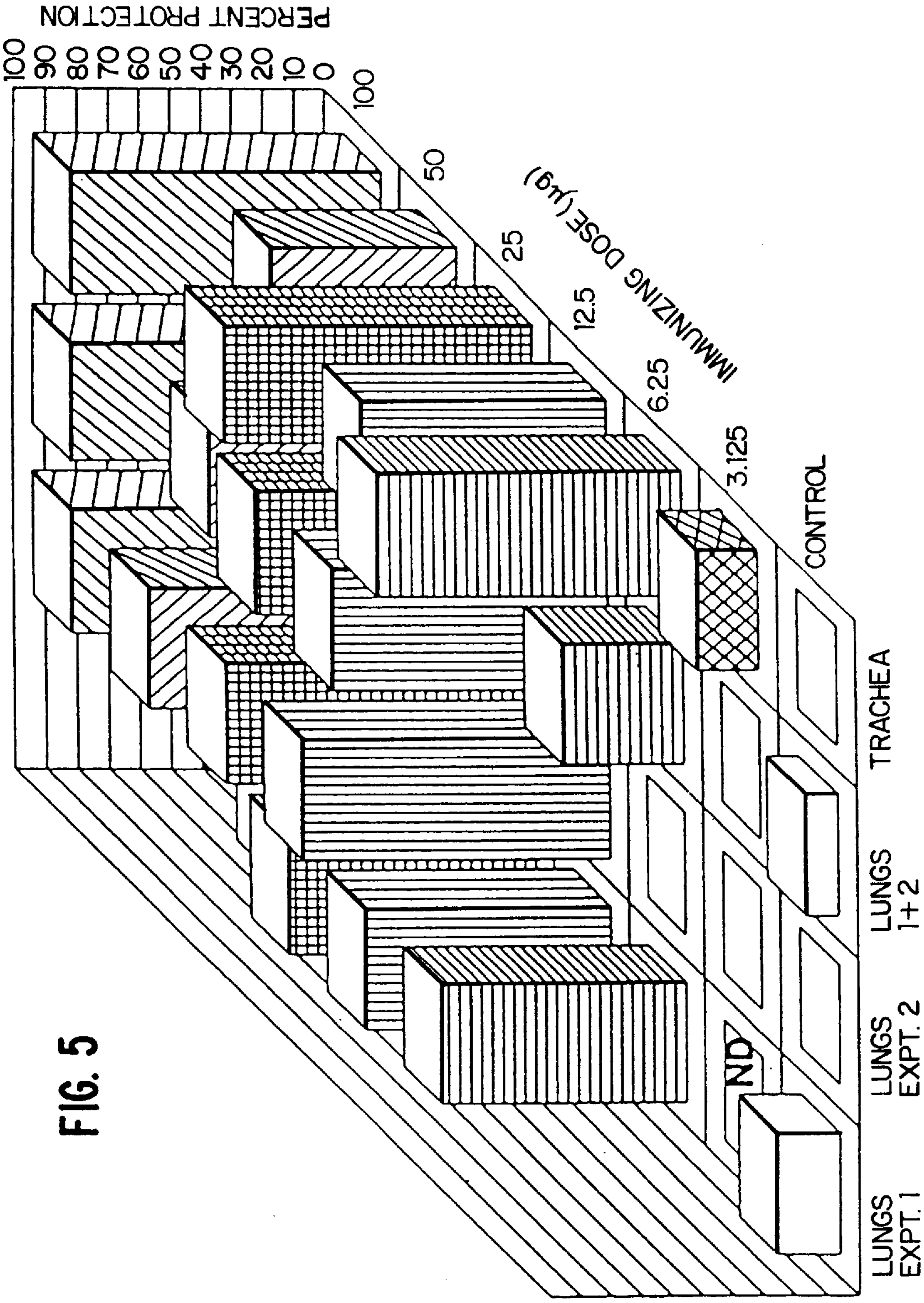
FIG. 5 is a graph showing the results of oral administration of polypeptide-cochleates when challenged with live virus.

The combined data for the two experiments is given in Table 1. The results also are shown graphically in FIG. 5.

TABLE 1

| Vaccine Dose µg Protein | Trachea[1] # infected/Total | Lungs[2] # Infected/Total | Lungs[3] # Infected/Total |
|---|---|---|---|
| 100 | 0/5 | 0/5 | 0/5 |
| 50 | 2/5 | 0/5 | 2/10 |
| 25 | 0/5 | 0/5 | 1/10 |
| 125 | 1/5 | 0/5 | 1/10 |
| 6.25 | 0/5 | 5/5 | 6/10 |
| 3.12 | 4/5 | 5/5 | 5/5 |
| 0 | 5/5 | 5/5 | 9/10 |

[1]Mice from Experiment B.
[2]Mice from Experiment B.
[3]Mice from Experiments A and B.

The data in Table 1 shows that all five of the unvaccinated mice had sufficient virus in the trachea to infect the embryonated chicken eggs (greater than $10^3$ particles per trachea or at least one egg infectious dose (EID) per 0.1 ml of suspension). In contrast, the oral vaccine provided a high degree of protection from viral replication in the trachea. All mice in groups 1, 3 and 5 of Experiment B were negative for virus. Two mice in group 2, 1 in group 4, and 4 in group 6 (the lowest vaccine dose) of Experiment B had sufficient virus to test positive in this very sensitive assay used to detect presence of virus.

The oral protein cochleate vaccine also provided protection against viral replication in the lungs. All twenty mice which received the four highest doses of vaccine were negative for virus when lung suspensions were cultured in embryonated chicken eggs (Table 1). All mice in the groups immunized with 6.25 µg and 3.1 µg glycoproteins and all mice in the unvaccinated control were positive for virus.

Even in the lowest two vaccine doses, there was some inhibition of viral replication. When lung suspensions were diluted 1/10 and inoculated into eggs, only one animal in the groups immunized with 6.25 µg was positive, as compared to three in the groups immunized with 3.12 µg and three in the unvaccinated control. Culturing of 1/100 dilutions resulted in one positive animal in each of the groups immunized with 6.25 and 3.12 µg, but 3 of 5 remained positive in the unvaccinated group. In addition, for the two animals in the group that was immunized with 3.12 µg, but which were negative at 1/100, only 50% of the eggs were infected at 1/10 and had low HA titers. In contrast, for the unvaccinated group, all eggs were infected and produced maximal amounts of virus at 1/10 and 1/100 dilutions.

Figure 6:
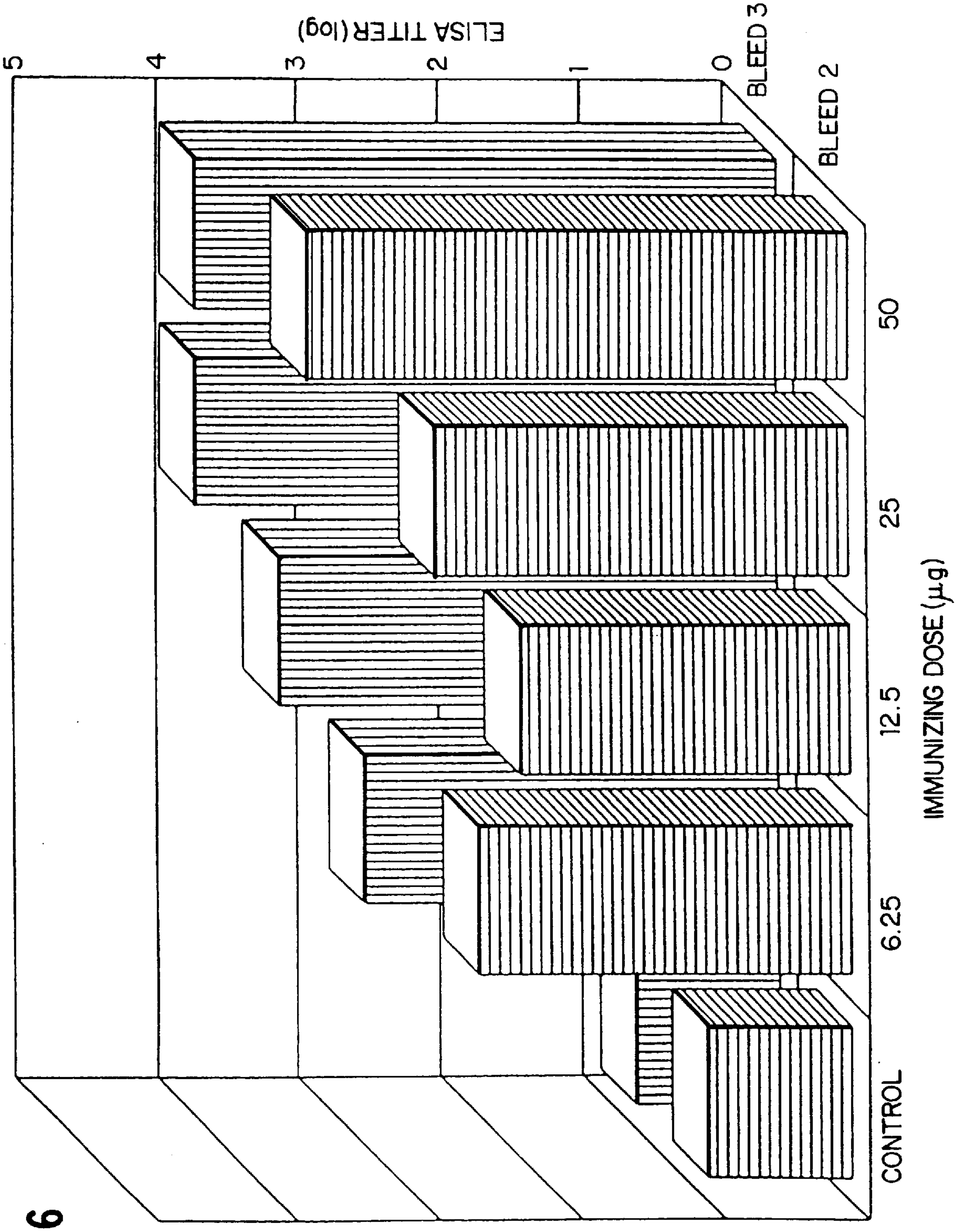
FIG. 6 is a graphic representation of serum antibody titers in mice following oral administration of Sendai-cochleates.

C57BL/6 mice were given cochleates containing Sendai virus glycoproteins orally at 0 and 3 weeks. They were bled at 0 (bleed 1), 3 (bleed 2), and 6 (bleed 3) weeks. Group 1 received approximately 50 µg protein, Group 2 about 25 µg, Group 3 about 12.5 µg, Group 4 about 6.25 µg, and Group 5 (negative control) received 0 µg protein. The levels of Sendai specific antibodies in the serum pooled from 5 mice in each dose group were determined by ELISA. The results are shown in FIG. 6. It can be seen that strong antibody responses were generated, that the magnitude of the response was directly related to the immunizing dose, and that the magnitude of the response increased (boosted) after a second immunization.

The response was extremely long-lived. The response is predominantly IgG, indicative of the involvement in T cell help and establishment of long-term memory cells associated with a secondary immune response. Surprisingly, the lowest dose which initially had the lowest response, now had the highest circulating antibody levels. This may be due to the immune system's down regulation of the very high responses originally but allowing the low response to slowly climb. This may also indicate a persistence and slow release of antigen. It is also interesting and consistent with the use of the oral route of immunization that significant IgA titers are generated and maintained.

Figure 7:
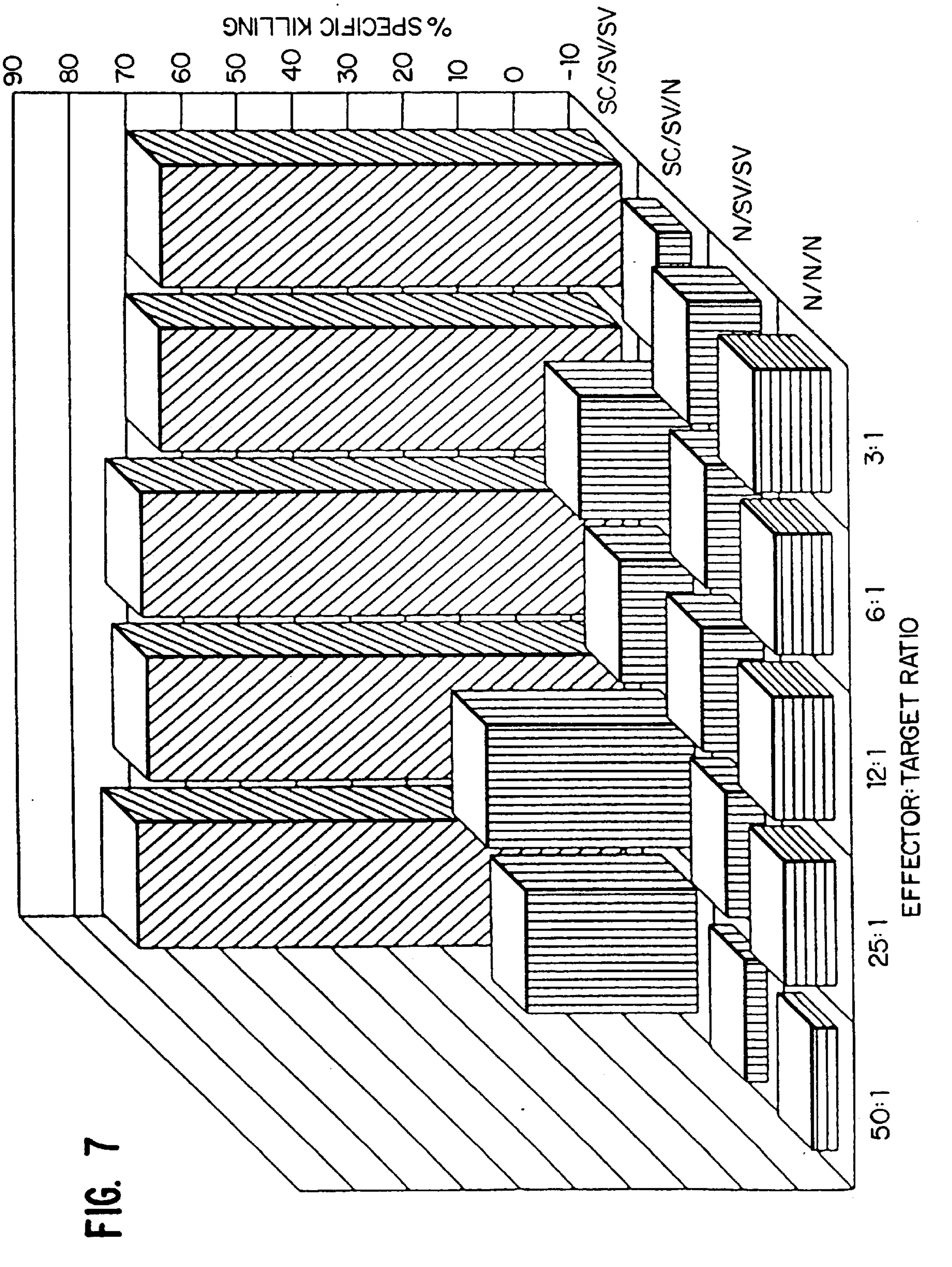
FIG. 7 is a graph depicting the induction of antigen-specific cytotoxic splenocytes following oral administration of Sendai cochleates.

A 50 µg protein dose of Sendai glycoprotein-containing cochleates was given orally. Two weeks later the animal (BALB/c mouse) was sacrificed and spleen cells obtained. Cytolytic activity of the spleen cells was measured by their ability to cause the release of chromium-51 from target cells presenting Sendai antigens. The non-immunized mouse did not kill Sendai virus (SV) pulsed cells with in culture restimulation (N/SV/SV) or non-Sendai presenting cells (N/N/N). (FIG. 7) In contrast, Sendai cochleate immunized mice killed SV pulsed targets to a very high degree and non-pulsed targets to a lesser degree. Cytolytic activity is crucial to clearance of cells infected with viruses, or intracellular parasites or to cancer cells. It is a highly desirable activity for a vaccine to induce, but classically has not been seen with most non-living vaccines. This is an important feature of protein-cochleate vaccines.

EXAMPLE 4

Eight week old BALB/c female mice were immunized IM twice with various polynucleotide-cochleate formulations, polynucleotide alone and controls and then splenocytes from the mice were tested for the ability to proliferate in response to a protein encoded by the polynucleotide.

Cochleates with and without fusogenic Sendai virus protein were prepared as described hereinabove. The polynucleotide used was the pCMVHIVLenv plasmid. The solution containing lipid and extracted Sendai virus envelop proteins as described hereinabove and polynucleotide were mixed at a 10:1 (w/w) ratio and 50:1 (w/w) ratio. That protocol yielded four groups, cochleate/DNA, 10:1; cochleate/DNA, 50:1; SV-cochleate/DNA, 10:1; and SV-cochleate/DNA, 50:1. Naked DNA was used at a rate of 10 µg/mouse and 50 µg/mouse. The control was buffer alone. Mice were immunized twice, 15 days apart at 50 µl/mouse.

Splenocytes were obtained and tested in a T-cell proliferation assay using tritiated thymidine, as known in the art. Control cultures contained no antigen or con A. The antigen used was p18 peptide, at 1 µM, 3 µM and 6 µM. Cells were harvested at days 2, 4 and 6 following preparation of the splenocyte cultures.

The naked DNA provided a marginal response above background. All four cochleate preparations yielded a p18-specific response which increased over time. At six days, the response was about four times above background.

The DNA concentration range at the 10:1 ratio was about 120–170 μg/ml. At the 50:1 (w/w) ratio; the DNA concentration was about 25–35 μg/ml.

The polynucleotide-cochleates were exposed to micrococcal nuclease and little or no nucleic acid degradation was observed.

The polynucleotide encapsulation efficiency was found to be about 50% based on quantification of free DNA from lipid, that is present in the supernatant following a precipitation reaction. After washing the precipitate and opening the structures by removing cation about 35% of the DNA was recovered.

EXAMPLE 5

In similar fashion, splenocytes from animals immunized as described in Example 4, were tested for antigen specific cytotoxic activity using a chromium release assay using labelled H-2 compatible target cells known to express an HIV protein, such as gp160. The responder cells can be stimulated by brief exposure to purified HIV peptides.

On prestimulation, animals exposed to polynucleotide cochleates demonstrated specific cytotoxic splenocytes directed to gp160, with nearly 100% cytotoxicity observed at an effector:target ratio of 100.

All references cited herein are incorporated by reference in entirety.

While the invention has been described in detail and with reference to specific embodiments thereof, it will be apparent to one skilled in the art that various changes and modifications can be made therein without departing from the spirit and scope thereof.

What is claimed is:

1. A protein- or peptide-cochleate formulation comprising a) a polynucleotide component;

b) a negatively charged lipid component, and c) a divalent cation component.

2. The protein- or peptide-cochleate formulation of claim 1, wherein said polynucleotide component is deoxyribonucleic acid.

3. The protein- or peptide-cochleate formulation of claim 2, wherein said deoxyribonucleic acid is transcribed to yield a ribonucleic acid.

4. The protein- or peptide-cochleate formulation of claim 3, wherein said ribonucleic acid is translated to yield a polypeptide.

5. The protein- or peptide-cochleate formulation of claim 1, wherein said polynucleotide component is ribonucleic acid.

6. The protein- or peptide-cochleate formulation of claim 1, wherein said lipid component is phospholipid.

7. The protein- or peptide-cochleate formulation of claim 6, wherein the phospholipid is selected from the group consisting of phosphatidylserine, phosphatidylglycerol, phosphatidylinositol, and phosphatidic acid.

8. The protein- or peptide-cochleate formulation of claim 1, wherein the divalent cation component is a cationic compound capable of chelating and completing negatively charged lipids.

9. The protein- or peptide-cochleate formulation of claim 8, wherein the divalent cation component i s selected from the group consisting of $Ca^{++}$, $Mg^{++}$, $Ba^{++}$ and $Zn^{++}$.

10. The protein- or peptide-cochleate formulation of claim 9, wherein the divalent cation component is $Ca^{++}$.

11. A method of administering a biologically relevant molecule to a cell in a host comprising administering a biologically effective amount of a cochleate formulation comprising a) a biologically relevant molecule component;

b) a negatively charged lipid component, and c) a divalent cation component.

12. The method of claim 11, wherein said biologically relevant molecule is a polynucleotide.

13. The method of claim 12, wherein said polynucleotide is deoxyribonucleic acid.

14. The method of claim 13, wherein said deoxyribonucleic acid is transcribed to yield a ribonucleic acid.

15. The method of claim 14, wherein said ribonucleic acid is translated to yield a polypeptide.

16. The method of claim 12, wherein said polynucleotide is ribonucleic acid.

17. The method of claim 12, wherein said lipid component is phospholipid.

18. The method of claim 17, wherein the phospholipid is selected from the group consisting of phosphatidylserine, phosphatidylglycerol, phosphatidylinositol, and phosphatidic acid.

19. The method of claim 12, wherein the divalent cation component is a cationic compound capable of chelating and completing negatively charged lipids.

20. The method of claim 19, wherein the divalent cation component is selected from the group consisting of $Ca^{++}$, $Mg^{++}$, $Ba^{++}$ and $Zn^{++}$.

21. The method of claim 20, wherein the divalent cation component is $Ca^{++}$.

22. The method of claim 12, wherein the polynucleotide is an antisense molecule.

23. The method of claim 11, wherein the biologically relevant molecule is a plasmid.

24. The method of claim 11, wherein the biologically relevant molecule is a nucleotide.

25. The protein- or peptide-cochleate formulation of claim 1, wherein the polynucleotide component is an antisense molecule.

26. The protein- or peptide-cochleate formulation of claim 1, wherein the polynucleotide component is a plasmid.

27. A protein- or peptide-cochleate formulation comprising a) a nucleotide component;

b) a negatively charged lipid component, and c) a divalent cation component.

* * * * *